United States Patent
Ishihara et al.

(10) Patent No.: US 12,070,316 B2
(45) Date of Patent: *Aug. 27, 2024

(54) WEARABLE ELECTRODE

(71) Applicants: NIPPON TELEGRAPH AND TELEPHONE CORPORATION, Tokyo (JP); TORAY INDUSTRIES, INC., Tokyo (JP)

(72) Inventors: Takako Ishihara, Tokyo (JP); Kazuhiko Takagahara, Tokyo (JP); Hiromi Takarada, Tokyo (JP); Emiko Ishikawa, Tokyo (JP); Masanobu Sato, Tokyo (JP); Yasuharu Murakami, Tokyo (JP)

(73) Assignees: NIPON TELEGRAPH AND TELEPHONE CORPORATION, Tokyo (JP); TORAY INDUSTRIES, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/190,656

(22) Filed: Mar. 27, 2023

(65) Prior Publication Data

US 2023/0225658 A1 Jul. 20, 2023

Related U.S. Application Data

(63) Continuation of application No. 16/344,726, filed as application No. PCT/JP2017/037344 on Oct. 16, 2017, now Pat. No. 11,660,034.

(30) Foreign Application Priority Data

Oct. 24, 2016 (JP) ................................. 2016-207639

(51) Int. Cl.
*A61B 5/00* (2006.01)
*A61B 5/24* (2021.01)
(Continued)

(52) U.S. Cl.
CPC ............. *A61B 5/282* (2021.01); *A61B 5/0006* (2013.01); *A61B 5/24* (2021.01); *A61B 5/25* (2021.01);
(Continued)

(58) Field of Classification Search
CPC ......... A61B 5/282; A61B 5/318; A61B 5/339; A61B 5/291; A61B 5/24; A61B 5/25; A61B 5/0006; A61B 5/6805; A61B 5/274
See application file for complete search history.

(56) References Cited

U.S. PATENT DOCUMENTS

| | | | |
|---|---|---|---|
| 6,047,203 | A | 4/2000 | Sackner et al. |
| 2004/0267145 | A1 | 12/2004 | David et al. |

(Continued)

FOREIGN PATENT DOCUMENTS

| | | |
|---|---|---|
| CN | 201710355 U | 1/2011 |
| JP | 2002-507131 A | 3/2002 |
| JP | 2013-528070 A | 7/2013 |

OTHER PUBLICATIONS

Communication about intention to grant a European patent received for European Application No. 17866111.2, mailed on Mar. 21, 2022, 6 pages.

(Continued)

*Primary Examiner* — Adam Z Minchella
(74) *Attorney, Agent, or Firm* — WOMBLE BOND DICKINSON (US) LLP (57) ABSTRACT

A wearable electrode includes an electrode (203) fixed to garment (21) such that the electrode (203) can simultaneously come in contact with the skin of respective parts from the ventral side to the dorsal side of the upper left part of the body of a wearer (20), and an electrode (204) fixed to the garment such that the electrode (204) can simultaneously come in contact with the skin of respective parts from the (Continued)

ventral side to the dorsal side of the upper right part of the body of the wearer (20). The electrodes (203, 204) are installed such that the attaching positions gradually descend from the ventral side to the dorsal side with the wearer (20) standing upright, or the attaching positions gradually ascend from the ventral side to the dorsal side with the wearer (20) standing upright.

6 Claims, 10 Drawing Sheets

(51) Int. Cl.
|  |  |
| --- | --- |
| *A61B 5/25* | (2021.01) |
| *A61B 5/282* | (2021.01) |
| *A61B 5/291* | (2021.01) |
| *A61B 5/318* | (2021.01) |
| *A61B 5/339* | (2021.01) |
| *A61B 5/274* | (2021.01) |

(52) U.S. Cl.
CPC .............. *A61B 5/291* (2021.01); *A61B 5/318* (2021.01); *A61B 5/339* (2021.01); *A61B 5/6805* (2013.01); *A61B 5/274* (2021.01)

(56) References Cited

U.S. PATENT DOCUMENTS

| | | | |
|---|---|---|---|
| 2005/0043640 A1* | 2/2005 | Chang | A61B 5/303 |
| | | | 600/509 |
| 2008/0287769 A1 | 11/2008 | Kurzweil et al. | |
| 2010/0198043 A1* | 8/2010 | Holzer | A41D 13/1281 |
| | | | 600/388 |
| 2011/0004088 A1 | 1/2011 | Grossman | |
| 2011/0288605 A1* | 11/2011 | Kaib | A61B 5/0816 |
| | | | 607/5 |
| 2014/0012145 A1 | 1/2014 | Kurzweil et al. | |
| 2014/0296682 A1 | 10/2014 | Wada et al. | |
| 2016/0374615 A1 | 12/2016 | Tsukada et al. | |

OTHER PUBLICATIONS

Decision to grant a European patent received for European Application No. 17866111.2, mailed on Aug. 4, 2022, 3 pages.
Hashimoto, Shoji, "Introduction to Nursing", Mechanism and Work of Human Body, 2013, 17 pages of Original Document Only.
International Preliminary Report on Patentability received for PCT Patent Application No. PCT/JP2017/037344, mailed on May 9, 2019, 23 pages (15 pages of English Translation and 8 pages of Original Document).
International Search Report and Written Opinion received for PCT Patent Application No. PCT/JP2017/037344, mailed on Dec. 12, 2017, 25 pages (15 pages of English Translation and 10 pages of Original Document).
Nakayama et al.,"The Prevalence of J Waves in the Additional Right Precordial Leads and Posterior Leads", Japanese Journal of Electrocardiology, vol. 32 No. 3, 2012, pp. 221-228 (English Abstract Submitted).
Office Action received for CA Patent Application No. 3041462, mailed on May 4, 2020, 5 pages.
Office Action received for Chilean Patent Application No. 2019-001073, mailed on Apr. 13, 2020, 28 pages (14 pages of English Translation and 14 pages of Office Action).
Office Action received for Japanese Patent Application No. 2018-547570, mailed on Aug. 27, 2019, 10 pages (5 pages of English Translation and 5 pages of Office Action).
Office Action received for Japanese Patent Application No. 2018-547570, mailed on Nov. 26, 2019, 6 pages (3 pages of English Translation and 3 pages of Office Action).
Ribeiro et al., "A Real time, Wearable ECG and Continuous Blood Pressure Monitoring System for First Responders", 33rd Annual International Conference of the IEEE EMBS, 2011, pp. 6894-6898.
Summons to attend oral proceedings pursuant to Rule 115(1) EPC received for European Patent Application No. 17866111.2, mailed on Sep. 7, 2021, 5 pages.
Supplementary European Search Report and Search Opinion received for EP Patent Application No. 17866111.2, mailed on Apr. 9, 2020, 7 pages.
Takano et al., "Guidelines for Management of Patient with ST-elevation myocardial infarction (JCS 2008)", 2006 to 2007 joint research reports, Japan Cardiology Association, Circulation Journal, vol. 72, Suppl.IV, 2008, pp. 1347-1442 (Original Document Only).

* cited by examiner

PRIOR ART

WEARABLE ELECTRODE

TECHNICAL FIELD

The present invention relates to a wearable electrode to be used to acquire a bioelectric signal such as an electrocardiographic waveform on a daily basis.

BACKGROUND ART

Recently, the importance of daily self-care of health is pointed out. One method of personal healthcare like this is to record and analyze bioelectric signals such as electrocardiographic waveforms for long time periods. This method is known to be able to find disturbances of autonomic nerves and symptoms of heart diseases in early stages, and effective in preventive medicine. A garment to which a biological electrode is attached (a wearable electrode) in order to acquire bioelectric signals for long periods of time is attracting attention (see non-patent literature 1).

RELATED ART LITERATURE

Non-Patent Literature

Non-Patent Literature 1: David M. D. Riberio, et al., "A Real time, Wearable ECG and Continuous Blood Pressure Monitoring System for First Responders", 33rd Annual International Conference of the IEEE EMBS, pp. 6894-6898, 2011

DISCLOSURE OF INVENTION

Problem to be Solved by the Invention

Figure 7A:
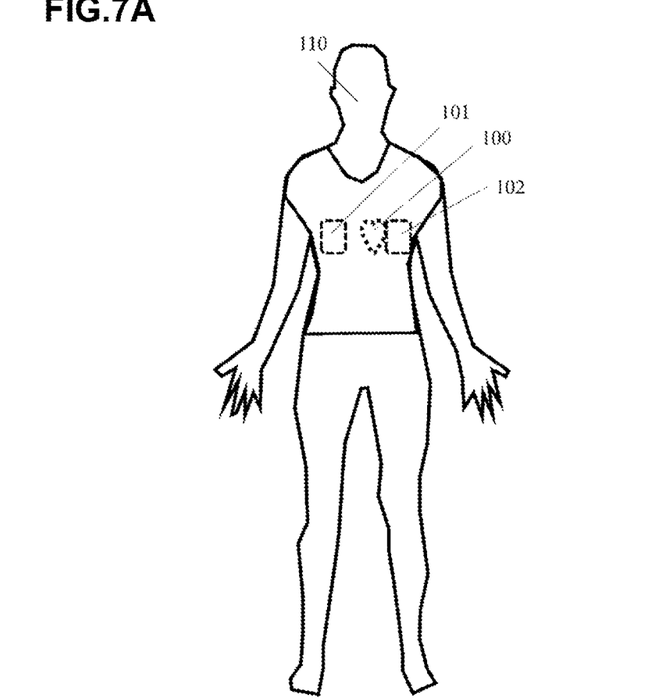
FIGS. 7A to 7C are schematic views showing the way a conventional wearable electrode is put on a human body.
Figure 7B:
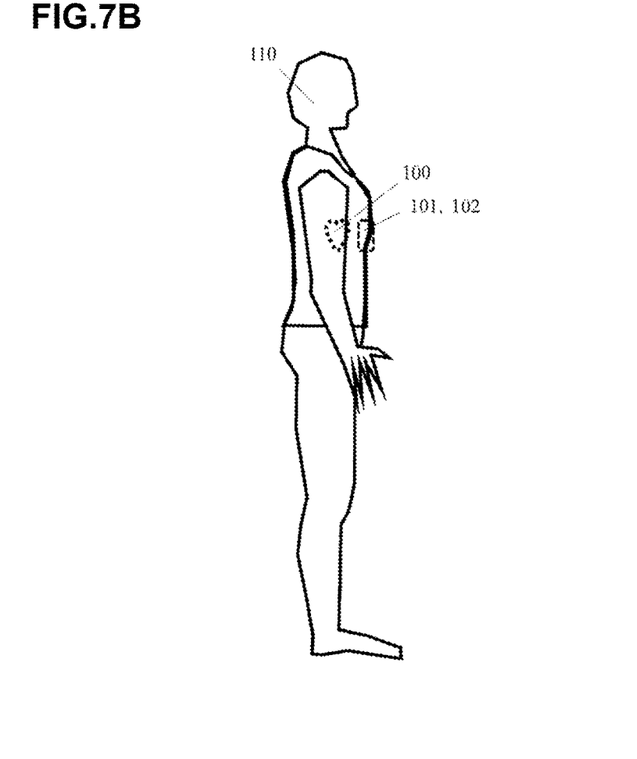
Figure 7C:
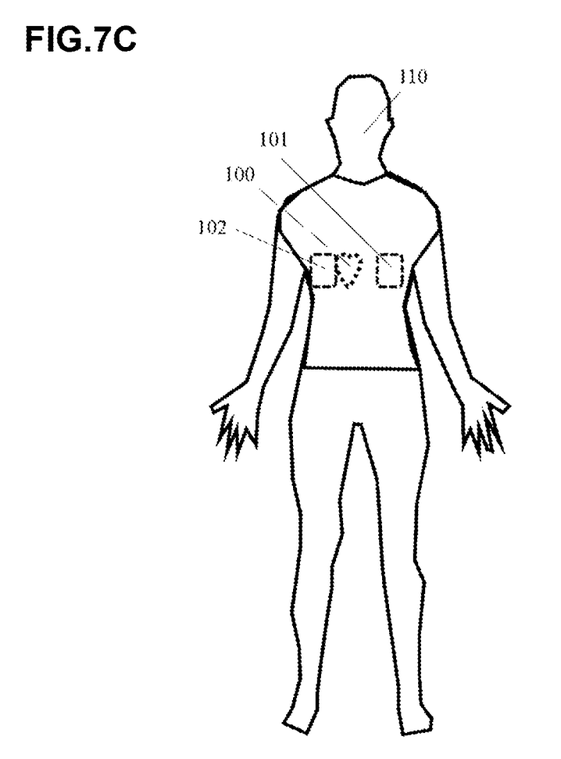

FIGS. 7A to 7C are schematic views showing the way a conventional wearable electrode is put on a human body. FIG. 7A is a human body front view, FIG. 7B is a human body side view, and FIG. 7C is a human body rear view. In the conventional wearable electrode as shown in FIGS. 7A to 7C, biological electrodes 101 and 102 are often installed in two, left and right portions of the chest at the height of the heart muscle of a heart 100 of a wearer 110 (this height is near the central line of the left ventricle, which is near the lower line of the nipple in the case of a male).

Such a conventional wearable electrode, however, has the following problems. That is, the biological electrodes 101 and 102 are sometimes detached from the body of the wearer when the wearer bends forward, so that measurement of bioelectric signals cannot be measured, or, the wearer feel unpleasant when the biological electrodes 101 and 102 are fastened on the body of the wearer by a flexible material so that the biological electrodes 101 and 102 do not leave the body.

It is an object of the present invention to provide a wearable electrode capable of reducing the unpleasant feeling of a wearer, and acquiring bioelectric signals even when the wearer takes various postures.

Means of Solution to the Problem

According to the present invention, a wearable electrode for detecting a bioelectric signal of a wearer of a garment is characterized by including one or more first electrodes fixed to the garment such that the first electrodes can simultaneously come in contact with skin of respective parts from a ventral side to a dorsal side of an upper left part of a body of the wearer, and one or more second electrodes fixed to the garment such that the second electrodes can simultaneously come in contact with skin of respective parts from a ventral side to a dorsal side of an upper right part of the body of the wearer, wherein the first electrodes and the second electrodes are installed such that attaching positions gradually descend from the ventral side to the dorsal side with the wearer standing upright, or the attaching positions gradually ascend from the ventral side to the dorsal side with the wearer standing upright.

Effect of the Invention

The present invention includes the first electrodes fixed to the garment such that the first electrodes can simultaneously come in contact with the skin of respective parts from the ventral side to the dorsal side of the upper left part of the body of the wearer, and the second electrodes fixed to the garment such that the second electrodes can simultaneously come in contact with the skin of respective parts from the ventral side to the dorsal side of the upper right part of the body of the wearer. Even when the wearer bends forward, therefore, the bioelectric signal of the wearer can be acquired because at least a part of each of the first and second electrodes come in contact with the body of the wearer. Also, the present invention can reduce the unpleasant feeling of the wearer because it is unnecessary to tighten the body of the wearer by the first and second electrodes. Furthermore, in the present invention, the first and second electrodes are installed such that the attaching positions gradually descend from the ventral side to the dorsal side with the wearer standing upright, or the attaching positions gradually ascend from the ventral side to the dorsal side with the wearer standing upright. Accordingly, it is possible to reduce an impediment to expansion and compression of the garment around the waist of the wearer caused by the first and second electrodes, and further reduce the unpleasant feeling of the wearer.

BEST MODE FOR CARRYING OUT THE INVENTION

The present invention will be explained below by referring to preferred embodiments, but the present invention is not limited to these embodiments.

First Embodiment

Figure 1A:
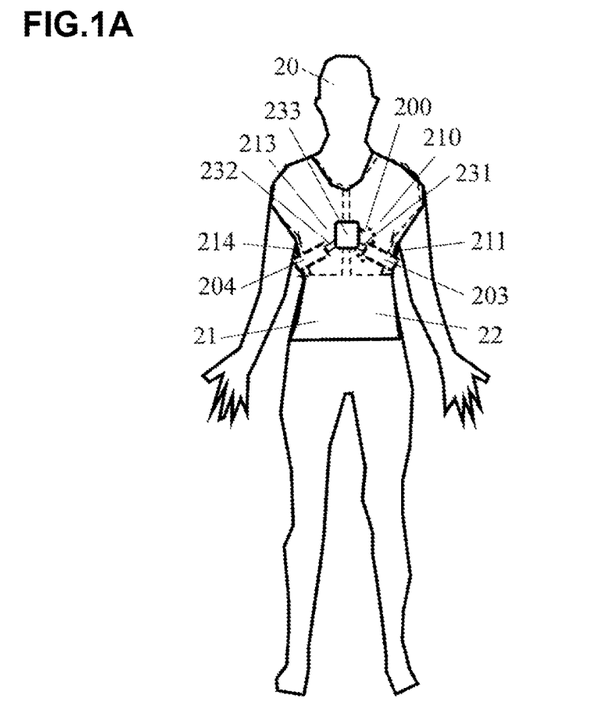
FIGS. 1A to 1C are schematic views showing the way a wearable electrode according to the first embodiment of the present invention is put on a human body.
Figure 1B:
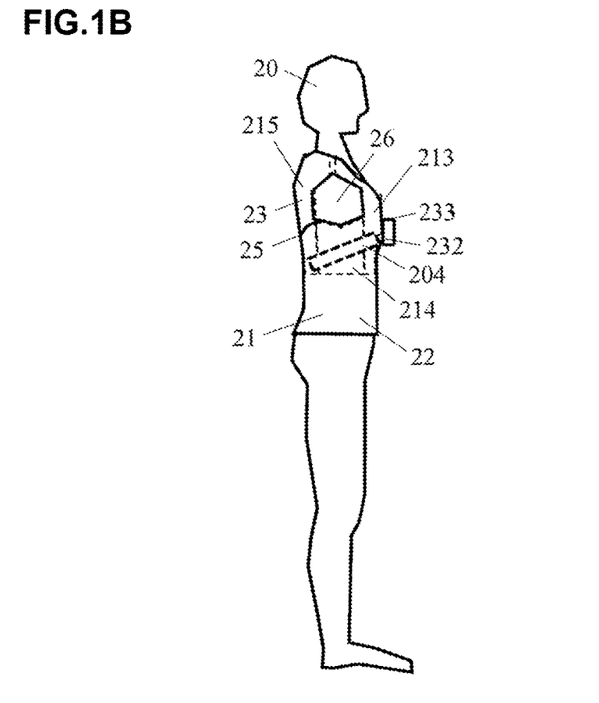
Figure 1C:
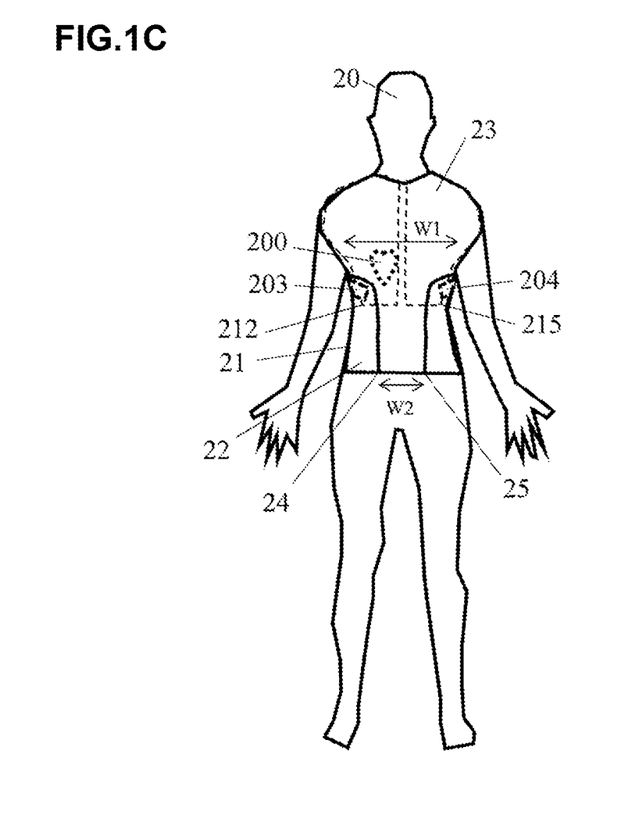

FIGS. 1A to 1C are schematic views showing the way a wearable electrode according to the first embodiment of the present invention is put on a human body. FIG. 1A is a front view of a human body, FIG. 1B is a side view of the human body, and FIG. 1C is a rear view of the human body. As shown in FIGS. 1A to 1C, the wearable electrode of this embodiment includes a garment 21, one or more belt-like electrodes 203, and one or more belt-like electrodes 204. The electrodes 203 are fixed to the inside of the garment 21 (the side in contact with the skin of a wearer 20 (a living body) of the garment 21), so that the electrodes 203 simultaneously come in contact with the skin of a left breast 210 of the wearer 20 of the garment 21, the skin of at least one (211 in FIG. 1A) of the left side chest, the left hypochondriac region, and the left armpit of the wearer 20, and the skin of at least one (212 in FIG. 1C) of the dorsal side of the left side chest, the dorsal side of the left hypochondriac region, and the lower portion of the left scapular region of the wearer 20, and the attaching positions gradually descend from the ventral side to the dorsal side with the wearer 20 standing upright. The electrodes 204 are fixed to the inside of the garment 21, so that the electrodes 204 simultaneously come in contact with the skin of a right breast 213 of the wearer 20 of the garment 21, the skin of at least one (214 in FIG. 1A) of the right side chest, the right hypochondriac region, and the right armpit of the wearer 20, and the skin of at least one (215 in FIG. 1C) of the dorsal side of the right side chest, the dorsal side of the right hypochondriac region, and the lower portion of the right scapular region of the wearer 20, and the attaching positions gradually descend from the ventral side to the dorsal side with the wearer 20 standing upright. FIGS. 1A to 1C also depict a heart 200 of the wearer 20.

Note that the armpit means a so-called underarm region, the side chest means a region below the armpit, and the hypochondriac region means a region below the side chest. Note also that the lower portion of the scapular region means a region below the scapular region having the scapula. The names of the individual parts of the human body are disclosed in, e.g., reference literature 'Shoji Hashimoto, "Introduction to Nursing 1 Mechanism and Work of Human Body", pp. 3-8, 2013'.

The electrodes 203 and 204 are respectively connected to a biological signal acquisition apparatus 233 by interconnections 231 and 232. Of the one or more electrodes 203 and the one or more electrodes 204, some of them are positive electrodes, and the rest are negative electrodes.

A material of the electrodes 203 and 204 is not particularly limited, and it is possible to unlimitedly use a carbon filler mixed resin, Ag cloth, conductive polymer impregnated fabric, and fabric impregnated with an electrolyte. The conductive polymer impregnated fabric is favorable because stimulation to the skin in a tight contact state is low and the durability is high. Also, the size of the electrodes 203 and 204 is not particularly limited as long as the installation conditions explained with reference to FIGS. 1A to 1C are met.

Note that a reference potential often used when receiving a bioelectric signal may also be obtained by installing an additional reference electrode on the garment 21 so that the reference electrode does not come in contact with the abovementioned positive and negative electrodes, and connecting the reference electrode to the biological signal acquisition apparatus 233 via an interconnection. In this case, of the one or more electrodes 203 separated from each other and the one or more electrodes 204 separated from each other, some are positive electrodes, and some are negative electrodes, and the electrode 203 or the electrode 204 other than the electrodes that function as the positive electrodes and the negative electrodes is the reference electrode.

Furthermore, the reference potential may also be an intermediate potential obtained from signals received by the positive electrode and the negative electrode, or the GND potential of the circuit of the biological signal acquisition apparatus 233.

The garment 21 is not particularly limited as long as the electrodes 203 and 204 can be installed, and it is possible to take forms such as a stomach band, a belt, and a corset, in addition to a shirt shown in FIGS. 1A to 1C.

When the garment 21 is a shirt as shown in FIGS. 1A to 1C, the body including a part below the neck and the scapular regions is wrapped up, so the electrodes 203 and 204 are arranged and maintained in more appropriate positions.

The electrodes 203 and 204 are arranged on the inside of a front body 22 of the garment 21. The electrodes 203 and 204 extend from the ventral side to the dorsal side so as to go round nearly the half of the body surface of the wearer 20. Accordingly, a part from the armpit to the abdomen of the front body 22 is extended toward the dorsal side from a center 26 of the armhole of the garment 21 so as to accommodate the dorsal-side distal ends of the electrodes 203 and 204. In accordance with this extension of the front body 22, therefore, a part from the armpit to the abdomen of a back body 23 of the garment 21 to be sewed up to the front body 22 is restricted in the direction of the posterior median line of the wearer 20 from the center 26 of the armhole, so a width W2 of this part is smaller than a body width W1. Consequently, sewing lines 24 and 25 of the front body 22 and the back body 23 are arranged nearer the dorsal side than the body-side barycentric line of the wearer 20.

As the material of the garment 21, it is possible to unlimitedly use natural fiber materials such as cotton and wool and synthetic fiber materials such as polyester and nylon used in ordinary clothes. However, the present invention is not limited to the shapes and materials of the garment 21 as described above.

Examples of the method of fixing the electrodes 203 and 204 to the garment 21 are a method of sewing the electrodes 203 and 204 to the garment 21, a method of adhering the electrodes 203 and 204 to the garment 21, and a method of impregnating the garment 21 with the electrodes 203 and 204. Of these methods, the adhesion method is particularly easy. It is also possible to bond the electrodes 203 and 204 to the front body 22 or the back body 23 of the garment 21 by thermocompression bonding by using an iron or a hot press machine before sewing the garment 21, and sew the front body 22 and the back body 23 after that.

As the interconnections 231 and 232, although well-known wiring materials can unlimitedly be used, it is more desirable to use a flexible wiring material (e.g., conductive rubber), or a material having a flexible structure or layout such as a spring, since the interconnections 231 and 232 are installed on the garment 21 which deforms in accordance with the motion of the wearer 20.

Also, the interconnections 231 and 232 are desirably covered with an insulator so as not to acquire signals from, e.g., the human body other than the electrode installation portions. Like the electrodes 203 and 204, the interconnections 231 and 232 are fixed to the front body 22 of the garment 21 such that the attaching positions gradually descend from the end portions on the side of the biological signal acquisition apparatus 233 to the end portions on the side of the electrodes 203 and 204, with the wearer 20 standing upright. Examples of the method of fixing the interconnections 231 and 232 to the garment 21 are a method of sewing the interconnections 231 and 232 to the garment 21, and a method of adhering the interconnections 231 and 232 to the garment 21.

In this embodiment, the electrodes 203 and 204 do not cross the sewing lines 24 and 25 because the electrodes 203 and 204 and the interconnections 231 and 232 are fixed to the front body 22 of the garment 21. As a consequence, the garment 21 fits the three-dimensional body structure, and the electrodes 203 and 204 hardly get out of positions. In addition, the electrodes 203 and 204 and the interconnections 231 and 232 can be installed on the front body 22 before sewing the garment 21, and this facilitates the sewing step.

The biological signal acquisition apparatus 233 acquires and processes a bioelectric signal (in this embodiment, an electrocardiographic waveform) detected by the electrodes 203 and 204. As the biological signal acquisition apparatus 233, it is possible to unlimitedly use a well-known apparatus that acquires an electrocardiographic waveform and detects an R wave. The biological signal acquisition apparatus 233 has a function of detecting the heartbeat from the electrocardiographic waveform, various display functions, and a function of wirelessly transmitting the acquired bioelectric signal and heartbeat information to the outside. Also, the biological signal acquisition apparatus 233 can be fixed on either the inside or the outside (the side opposite to the side in contact with the skin of the wearer 20) of the garment 21.

In this embodiment as described previously, however, the positions of the end portions of the interconnections 231 and 232 on the side of the electrodes 203 and 204 must be obliquely below the positions of the end portions of the interconnections 231 and 232 on the side of the biological signal acquisition apparatus 233, with the wearer 20 standing upright. Therefore, the position of the biological signal acquisition apparatus 233 must be determined so as to implement the layout of the interconnections 231 and 232 like this.

Figure 2:
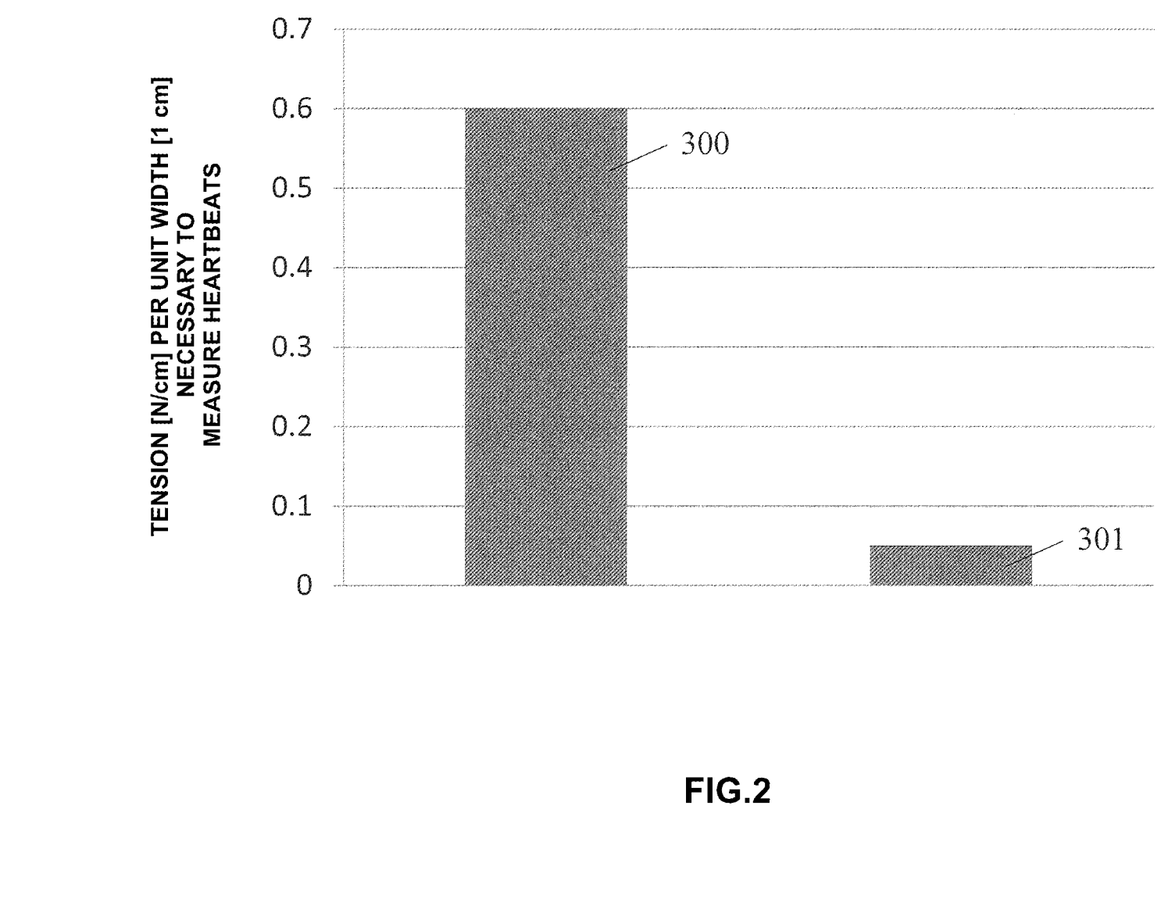
FIG. 2 is a graph showing the tension per unit width of the chest, which is necessary to measure the heartbeat, when using the wearable electrode according to the first embodiment of the present invention and a conventional wearable electrode.
Figure 3:
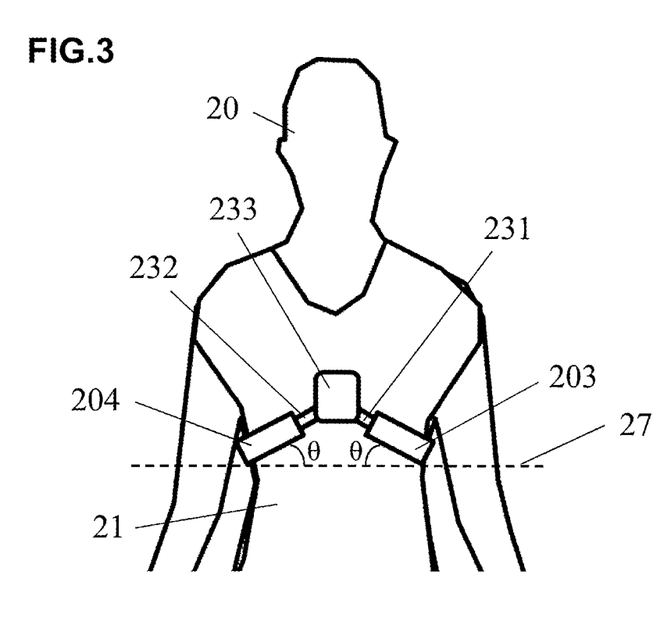
FIG. 3 is a view for explaining an example of a method of putting the wearable electrode according to the first embodiment of the present invention on a human body.

FIG. 2 shows the results of measurement of the tension of the chest necessary to measure the heartbeat, when the same wearer wore the conventional wearable electrode (FIG. 7) in which electrodes were installed in two, left and right portions of the chest at the height of the heart of the wearer and the wearable electrode of this embodiment in turn, and walked at 4 km per hour. In FIG. 2, the lowest value of the tension per unit width (1 cm) around the waist when normal heartbeat measurement was successful is taken as the measurement result. Also, as shown in FIG. 3, the electrodes 203 and 204 of the wearable electrode of this embodiment made an angle θ of 30° with a horizontal plane 27 when the wearer 20 was standing upright.

Referring to FIG. 2, tension 300 was necessary to measure the heartbeat when using the conventional wearable electrode, and tension 301 was necessary to measure the heartbeat when using the wearable electrode of this embodiment. As shown in FIG. 2, compared to the conventional wearable electrode, this embodiment reduces the tension of the chest necessary to measure the heartbeat, and hence can reduce the unpleasant feeling of the wearer.

Figure 4:
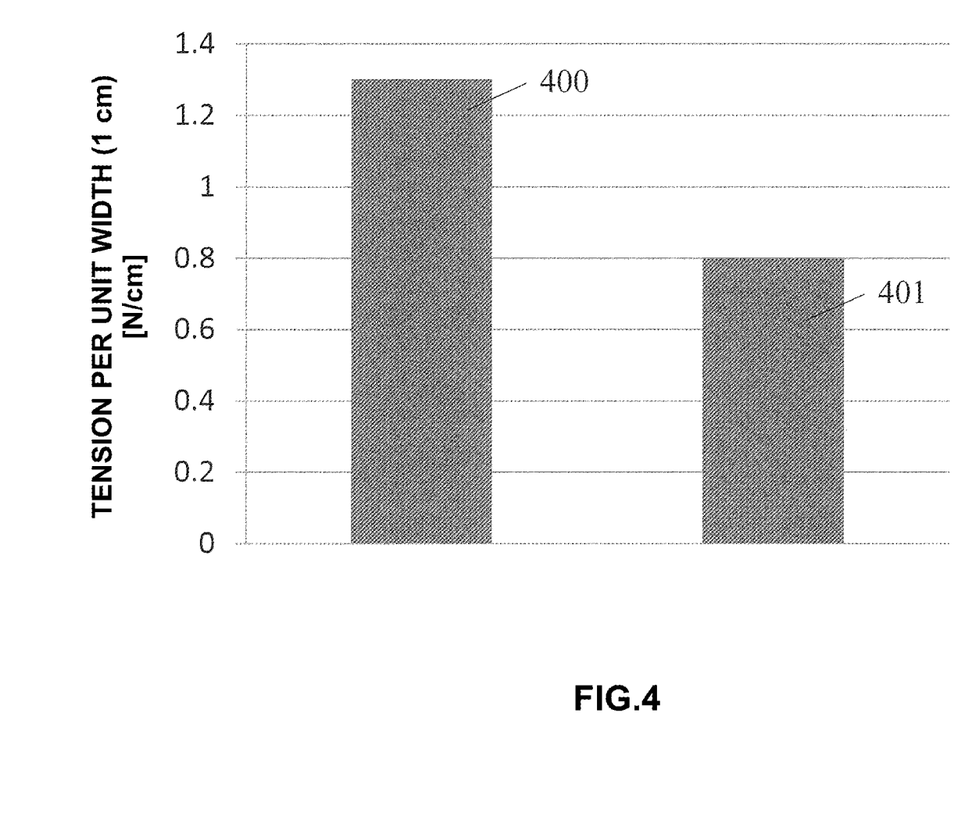
FIG. 4 is a graph showing the tension per unit width of the chest, which is necessary to measure the heartbeat, when using the wearable electrode according to the first embodiment of the present invention and a wearable electrode in which electrodes are horizontally arranged.
Figure 5:
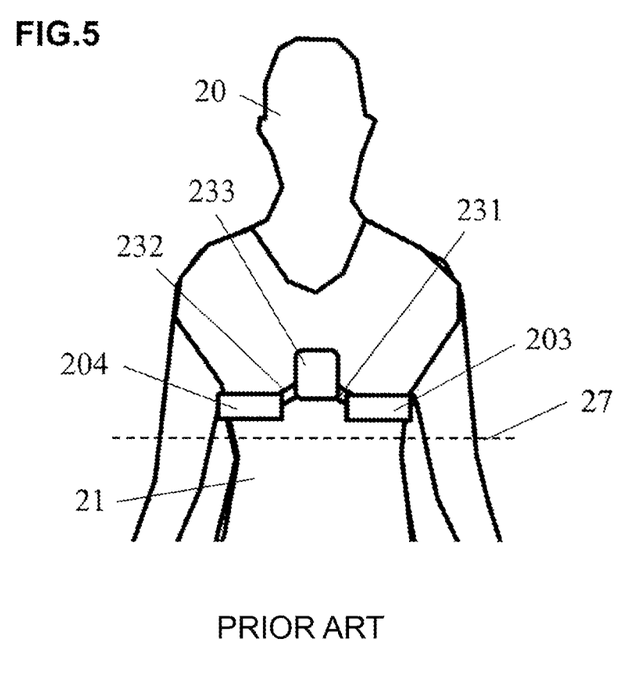
FIG. 5 is a view for explaining the wearable electrode in which the electrodes are horizontally arranged.

FIG. 4 shows the results of measurement of the tension of the chest when the same wearer wore the wearable electrode in which the electrodes 203 and 204 were horizontally arranged on the garment 21 and the wearable electrode of this embodiment in turn. In FIG. 4, the tension per unit width (1 cm) around the waist when the around-the-waist dimension of the chest on which the electrodes 203 and 204 were arranged was extended by 20% is taken as the measurement result. As shown in FIG. 3, the electrodes 203 and 204 of the wearable electrode of this embodiment made an angle θ of 30° with the horizontal line 27 when the wearer 20 was standing upright. As shown in FIG. 5, the wearable electrode in which the electrodes 203 and 204 are horizontally arranged is an electrode in which the horizontal plane 27 and the extending direction of the electrodes 203 and 204 are parallel (θ is 0°) when the wearer 20 was standing upright.

Referring to FIG. 4, tension 400 was obtained when using the wearable electrode in which the electrodes 203 and 204 were horizontally arranged, and tension 401 was obtained when using the wearable electrode of this embodiment.

FIG. 4 shows that this embodiment can reduce the tension of the chest and the unpleasant feeling of the wearer by obliquely installing the electrodes 203 and 204, compared to the wearable electrode in which the electrodes 203 and 204 are horizontally installed.

In this embodiment as described above, the electrode 203 is so installed as to simultaneously come in contact with the skin in respective parts from the ventral side to the dorsal side of the upper left part of the body of the wearer, and the electrode 204 is so installed as to simultaneously come in contact with the skin in respective parts from the ventral side to the dorsal side of the upper right part of the body of the wearer. Even when the wearer is bending forward, therefore, at least a part of each of the electrodes 203 and 204 comes in contact with the body of the wearer, so the bioelectrical signal of the wearer can be acquired. Also, this embodiment does not adopt a structure that tightens the body of the wearer by the electrodes 203 and 204, and hence can reduce the unpleasant feeling of the wearer. Furthermore, the electrodes 203 and 204 and the interconnections 231 and 232 are installed obliquely to the horizontal plane with the wearer standing upright. Therefore, even when materials having flexibility lower than that of the material of the garment 21 are used as the electrodes 203 and 204 and the interconnections 231 and 232, it is possible to reduce an impediment to expansion and contraction of the garment 21 around the waist caused by the electrodes 203 and 204 and the interconnections 231 and 232, and reduce the unpleasant feeling of the wearer.

Second Embodiment

Figure 6A:
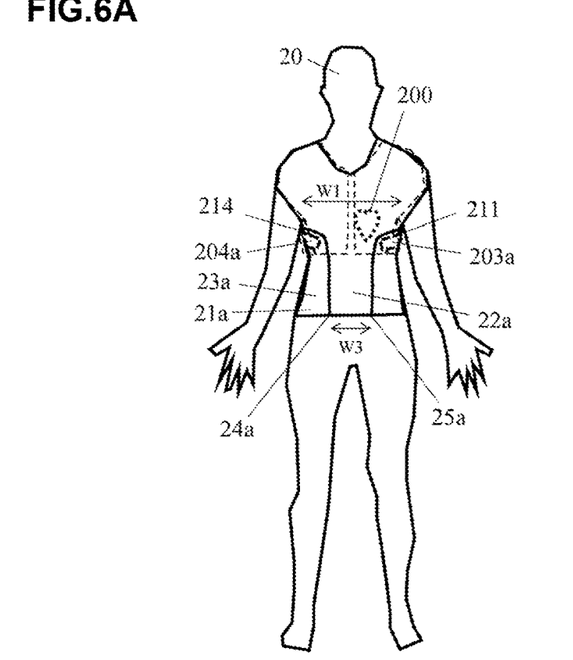
FIGS. 6A to 6C are schematic views showing the way a wearable electrode according to the second embodiment of the present invention is put on a human body.
Figure 6B:
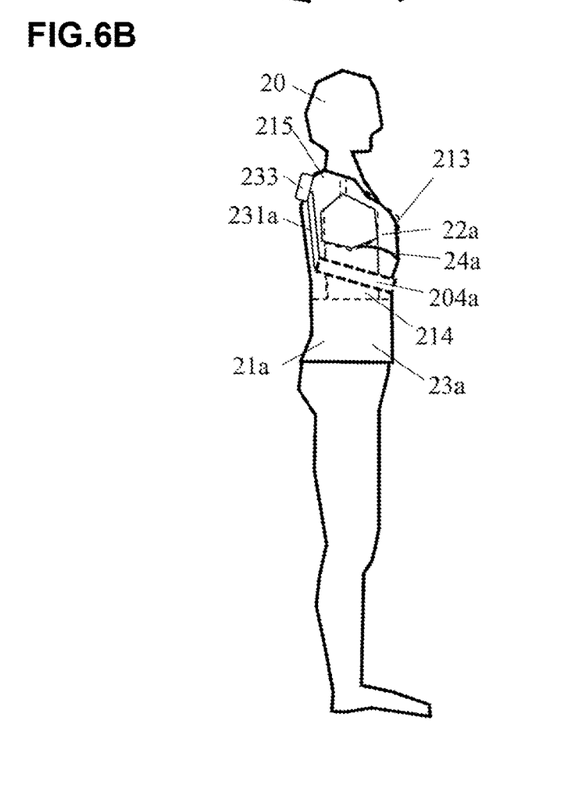
Figure 6C:
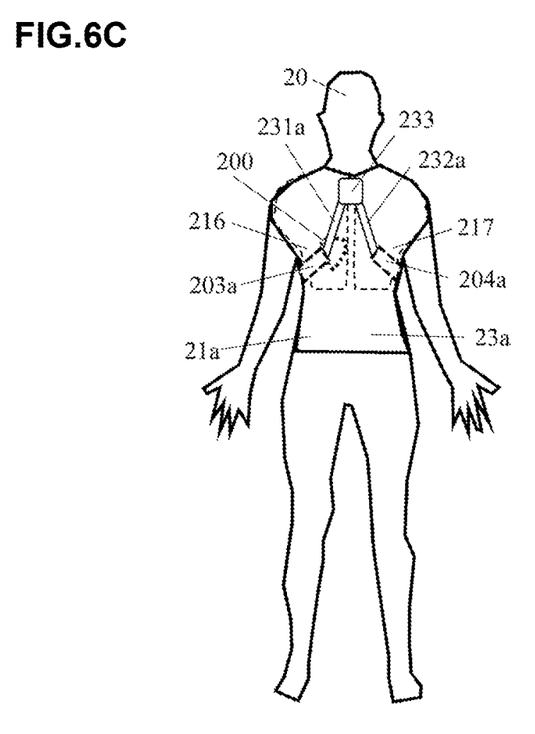

Next, the second embodiment of the present invention will be explained. FIGS. 6A to 6C are schematic views showing the way a wearable electrode according to the second embodiment of the present invention is put on a human body. FIG. 6A is a human body front view, FIG. 6B is a human body side view, and FIG. 6C is a human body rear view. As shown in FIGS. 6A to 6C, the wearable electrode of this embodiment includes a garment 21a, one or more belt-like electrodes 203a, and one or more belt-like electrodes 204a. The electrodes 203a are fixed to the inside of the garment 21a, so that the electrodes 203 simultaneously come in contact with the skin of at least one of the ventral side of the left side chest and the ventral side of the left hypochondriac region of a wearer 20 of the garment 21a, the skin of at least one (211 in FIG. 6A) of the left side chest, the left hypochondriac region, and the left armpit of the wearer 20, and the skin of at least one (216 in FIG. 6C) of the dorsal side of the left side chest and the left scapular region of the wearer 20, and the attaching positions gradually ascend from the ventral side to the dorsal side with the wearer 20 standing upright. The electrodes 204a are fixed to the inside of the garment 21a, so that the electrodes 204a simultaneously come in contact with the skin of at least one of the ventral side of the right side chest and the ventral side of the right hypochondriac region of the wearer 20 of the garment 21a, the skin of at least one (214 in FIG. 6A) of the right side chest, the right hypochondriac region, and the right armpit of the wearer 20, and the skin of at least one (217 in FIG. 6C) of the dorsal side of the right side chest and the right scapular region of the wearer 20, and the attaching positions gradually ascend from the ventral side to the dorsal side with the wearer 20 standing upright.

The electrodes 203a and 204a are respectively connected to a biological signal acquisition apparatus 233 by interconnections 231a and 232a. When using a reference electrode, the electrode 203a or 204a other than the electrodes 203a and 204a that function as positive electrodes and negative electrodes can be used as the reference electrode, as in the first embodiment.

The electrodes 203a and 204a are made of the same material as the electrodes 203 and 204 of the first embodiment, but are arranged on the inside of a back body 23a of the garment 21a. In this embodiment, the electrodes 203a and 204a extend from the dorsal side to the ventral side so as to go round nearly the half of the body surface of the wearer 20. Accordingly, a part from the armpit to the abdomen of the back body 23a is extended toward the ventral side from a center 26 of the armhole of the garment 21a so as to accommodate the ventral-side distal ends of the electrodes 203a and 204a. In accordance with this extension of the back body 23a, therefore, a part from the armpit to the abdomen of a front body 22a of the garment 21a to be sewed up to the back body 23a is restricted in the direction of the anterior median line of the wearer 20 from the center 26 of the armhole, so a width W3 of this part is smaller than a body width W1. Consequently, sewing lines 24a and 25a of the front body 22a and the back body 23a are arranged nearer the ventral side than the body-side barycentric line of the wearer 20.

Like the electrodes 203a and 204a, the interconnections 231a and 232a are fixed to the back body 23a of the garment 21a such that the attaching positions gradually descend from the end portions on the side of the biological signal acquisition apparatus 233 to the end portions on the side of the electrodes 203a and 204a, with the wearer 20 standing upright.

In this embodiment, the electrodes 203a and 204a do not cross the sewing lines 24a and 25a because the electrodes 203a and 204a and the interconnections 231a and 232a are fixed to the back body 23a of the garment 21a. As a consequence, the garment 21a fits the three-dimensional body structure, and the electrodes 203a and 204a hardly get out of positions. In addition, the electrodes 203a and 204a and the interconnections 231a and 232a can be installed on the back body 23a before sewing the garment 21a, and this facilitates the sewing step. Furthermore, in this embodiment, the interconnections 231 and 232 and the biological signal acquisition apparatus 233 need not be installed on the ventral side. Accordingly, the garment 21a can be front-open garment, and this can facilitate dressing and undressing.

In the first embodiment and this embodiment, the method of fixing the electrodes 203, 203a, 204, and 204a and the interconnections 231, 231a, 232, and 232a to the front body 22 or the back body 23a is not particularly limited, and an arbitrary method can be used. Especially when performing fixation by thermocompression bonding, if the electrodes 203, 203a, 204, and 204a and the interconnections 231, 231a, 232, and 232a do not cross the sewed portions as in the first embodiment and this embodiment, the compression-bonding surface is flat, so the front body or back body before sewing in which members to be compression-bonded are arranged can be placed on the plate of a hot press machine normally used in thermocompression bonding. This not only facilitates forming the garment 21 and 21a, but also improves the durability of adhesion because the electrodes 203, 203a, 204, and 204a and the interconnections 231, 231a, 232, and 232a can evenly be adhered on the entire surface.

The function of the biological signal acquisition apparatus 233 is the same as explained in the first embodiment. In this embodiment, however, the positions of the end portions of the interconnections 231a and 232a on the side of the electrodes 203a and 204a must be obliquely below the positions of the end portions of the interconnections 231a and 232a on the side of the biological signal acquisition apparatus 233, with the wearer 20 standing upright. Therefore, the position of the biological signal acquisition apparatus 233 must be so determined as to be able to implement the layout of the interconnections 231a and 232a as described above.

The rest of the arrangement is the same as explained in the first embodiment. Thus, this embodiment can achieve the same effect as that of the first embodiment.

Note that in the first and second embodiments, the electrode shape is an almost rectangular shape in planar view when the electrode is not fixed to a garment but stretched flat. However, the present invention is not limited to this, and it is also possible to adopt an electrode shape that is an almost elliptical shape when the electrode is stretched flat.

Note also that the biological signal acquisition apparatus 233 may also have a structure that can detachably be attached to the garment 21 and 21a. In this case, the biological signal acquisition apparatus 233 and the interconnections 231, 231a, 232, and 232a are electrically connected via connectors.

INDUSTRIAL APPLICABILITY

The present invention is applicable to a technique of acquiring a bioelectric signal.

Explanation of the Reference Numerals and Signs

20 . . . wearer, 21, 21a . . . garment, 22, 22a . . . front body of a garment, 23, 23a . . . back body of garment, 24, 24a, 25, 25a . . . sewing line of front or back body, 26 . . . center of armhole, 200 . . . heart, 203, 203a, 204, 204a . . . electrode, 210 . . . left breast, 211 . . . at least one of left side chest, left hypochondriac region, and left armpit, 212 . . . at least one of dorsal side of left side chest, dorsal side of left hypochondriac region, and lower portion of left scapular region, 213 . . . right breast, 214 . . . at least one of right side chest, right hypochondriac region, and right armpit, 215 . . . at least one of dorsal side of right side chest, dorsal side of right hypochondriac region, and lower portion of right scapular region, 216 . . . at least one of dorsal side of left side chest and left scapular region, 217 . . . at least one of dorsal side of right side chest and right scapular region, 231, 231a, 232, 232a . . . interconnection, 233 . . . biological signal acquisition apparatus

The invention claimed is:

1. A wearable garment for detecting a bioelectric signal of a wearer, comprising:
   one or more first electrodes fixed to the garment such that the one or more first electrodes, when the wearable garment is worn, are configured to simultaneously come in contact with skin of parts from a ventral side to a dorsal side of an upper left part of a body of the wearer; and
   one or more second electrodes fixed to the garment such that the one or more second electrodes, when the wearable garment is worn, are configured to simultaneously come in contact with skin of parts from a ventral side to a dorsal side of an upper right part of the body of the wearer,
   wherein each of the one or more first electrodes and the one or more second electrodes includes a ventral-side distal end and a dorsal-side distal end and is configured to be installable obliquely to a horizontal plane of the garment from the ventral-side distal end to the dorsal-side distal end when the wearer stands upright,
   wherein each of the one or more first electrodes is installed such that, when the garment is worn, each of the one or more first electrodes is configured to simultaneously come in contact with skin of at least one of the ventral side of the left side chest and the ventral side of the left hypochondriac region of the wearer, skin of at least one of the left side chest, the left hypochondriac region, and the left armpit of the wearer, and skin of at least one of the dorsal side of the left side chest and the left scapular region of the wearer, and each of the one or more first electrodes ascends from the ventral-side distal end toward the dorsal-side distal end when the wearer stands upright, and
   wherein each of the one or more second electrodes is installed such that, when the garment is worn, each of the one or more second electrodes is configured to simultaneously come in contact with skin of at least one of the ventral side of the right side chest and the ventral side of the right hypochondriac region of the wearer, skin of at least one of the right side chest, the right hypochondriac region, and the right armpit of the wearer, and skin of at least one of the dorsal side of the right side chest and the right scapular region of the wearer, and each of the one or more second electrodes ascends from the ventral-side distal end toward the dorsal-side distal end when the wearer stands upright.

2. The wearable garment according to claim 1, comprising:
   a biological signal acquisition apparatus fixed to a dorsal side of the garment and configured to acquire a bioelectric signal of the wearer;
   a first interconnection including a first end portion connected to the biological signal acquisition apparatus and a second end portion connected to the one or more first electrodes; and
   a second interconnection including a third end portion connected to the biological signal acquisition apparatus and a fourth end portion connected to the one or more second electrodes,
   wherein the first interconnection is fixed to the garment such that the first interconnection descends from the first end portion toward the second end portion when the wearer stands upright, and
   the second interconnection is fixed to the garment such that the second interconnection descends from the third end portion toward the fourth end portion when the wearer stands upright.

3. The wearable garment according to claim 2, comprising:
   a front body; and
   a back body sewed up to the front body,
   wherein sewing lines of the front body and the back body are arranged nearer the ventral side than a body-side barycentric line of the wearer, when the wearable garment is worn, and
   the one or more first electrodes, the one or more second electrodes, the first interconnection, and the second interconnection are fixed to the back body.

4. The wearable garment according to claim 3, wherein the one or more first electrodes include first electrodes,
   the one or more second electrodes include second electrodes,
   the first electrodes are separated from each other,
   the second electrodes are separated from each other,
   the first electrodes include at least one positive electrode, at least one negative electrode, and at least one reference electrode, and
   the second electrodes include at least one positive electrode, at least one negative electrode, and at least one reference electrode.

5. The wearable garment according to claim 2, wherein the one or more first electrodes include first electrodes,
   the one or more second electrodes include second electrodes,
   the first electrodes are separated from each other,
   the second electrodes are separated from each other,
   the first electrodes include at least one positive electrode, at least one negative electrode, and at least one reference electrode, and
   the second electrodes include at least one positive electrode, at least one negative electrode, and at least one reference electrode.

6. The wearable garment according to claim 1, wherein the one or more first electrodes include first electrodes,
   the one or more second electrodes include second electrodes,
   the first electrodes are separated from each other,
   the second electrodes are separated from each other,
   the first electrodes include at least one positive electrode, at least one negative electrode, and at least one reference electrode, and
   the second electrodes include at least one positive electrode, at least one negative electrode, and at least one reference electrode.

* * * * *

UNITED STATES PATENT AND TRADEMARK OFFICE
CERTIFICATE OF CORRECTION

| | | |
|---|---|---|
| PATENT NO. | : 12,070,316 B2 | Page 1 of 1 |
| APPLICATION NO. | : 18/190656 | |
| DATED | : August 27, 2024 | |
| INVENTOR(S) | : Takako Ishihara et al. | |

It is certified that error appears in the above-identified patent and that said Letters Patent is hereby corrected as shown below:

On the Title Page

In Item (73), delete:
"Assignees: NIPPON TELEGRAPH AND TELEPHONE CORPORATION, Tokyo (JP);
TORAY INDUSTRIES, INC., Tokyo (JP)"
And insert:
--Assignee: NIPPON TELEGRAPH AND TELEPHONE CORPORATION, Tokyo (JP)--

Signed and Sealed this
Thirty-first Day of December, 2024

Derrick Brent
*Acting Director of the United States Patent and Trademark Office*